United States Patent
Higashiyama et al.

(10) Patent No.: US 10,716,913 B2
(45) Date of Patent: Jul. 21, 2020

(54) CUFF-PRESSURE CONTROL DEVICE, CUFFED TRACHEAL TUBE, RESPIRATOR, AND OBSTRUCTION DETECTION METHOD

(71) Applicant: Murata Manufacturing Co., Ltd., Kyoto (JP)

(72) Inventors: Yuzo Higashiyama, Kyoto (JP); Sho Makino, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 830 days.

(21) Appl. No.: 15/431,949

(22) Filed: Feb. 14, 2017

(65) Prior Publication Data

US 2017/0151403 A1  Jun. 1, 2017

Related U.S. Application Data

(63) Continuation of application No. PCT/JP2015/072032, filed on Aug. 4, 2015.

(30) Foreign Application Priority Data

Aug. 20, 2014 (JP) .................... 2014-167550

(51) Int. Cl.
| | | |
|---|---|---|
| *A61M 16/04* | (2006.01) | |
| *A61M 16/20* | (2006.01) | |
| *A61M 16/00* | (2006.01) | |

(52) U.S. Cl.
CPC .......... *A61M 16/044* (2013.01); *A61M 16/04* (2013.01); *A61M 16/202* (2014.02); (Continued)

(58) Field of Classification Search
CPC .............. A61M 16/00; A61M 16/0003; A61M 16/0051; A61M 16/021; A61M 16/022; (Continued)

(56) References Cited

U.S. PATENT DOCUMENTS 5,681,339 A * 10/1997 McEwen ............ A61B 17/1355
606/201
2009/0229605 A1  9/2009 Efrati et al.
(Continued)

FOREIGN PATENT DOCUMENTS

| JP | 4175664 B2 | 11/2008 |
|---|---|---|
| JP | 2009-505715 A | 2/2009 |

(Continued)

OTHER PUBLICATIONS

International Search Report for PCT/JP2015/072032 dated Sep. 1, 2015.
Written Opinion for PCT/JP2015/072032 dated Sep. 1, 2015.

*Primary Examiner* — Timothy A Stanis
*Assistant Examiner* — Matthew Standard
(74) *Attorney, Agent, or Firm* — Pearne & Gordon LLP (57) ABSTRACT

A cuff-pressure control device includes a pump supplying gas into the cuff, a connection path connecting the pump and the cuff, an exhaust valve exhausting gas in the cuff through the connection path, a pressure sensor measuring an internal pressure of the connection path, and a controller controlling the internal pressure of the cuff according to a measured value of the internal pressure of the connection path measured with the pressure sensor. The controller includes an obstruction detection unit that obtains, from the measured value of the pressure sensor, a pressure change amount from a time point when the pump is stopped while the internal pressure of the connection path is being increased by the pump to a time point after a predetermined time elapses and that detects the obstruction of the connection tube when the pressure change amount is less than or equal to a predetermined threshold value.

15 Claims, 6 Drawing Sheets

(52) U.S. Cl.
CPC ............... *A61M 2016/0027* (2013.01); *A61M 2205/3344* (2013.01)

(58) Field of Classification Search
CPC .. A61M 16/024; A61M 16/026; A61M 16/04; A61M 16/0402; A61M 16/0434; A61M 16/044; A61M 16/045; A61M 16/0454; A61M 16/0461; A61M 16/0465; A61M 2205/33; A61M 2205/3327; A61M 2205/3331; A61M 2205/3334; A61M 2205/50

See application file for complete search history.

(56) References Cited

U.S. PATENT DOCUMENTS

| | | |
|---|---|---|
| 2011/0265795 A1 | 11/2011 | Tagawa et al. |
| 2013/0014756 A1 | 1/2013 | Young et al. |
| 2013/0228172 A1 | 9/2013 | Young et al. |

FOREIGN PATENT DOCUMENTS

| | | |
|---|---|---|
| JP | 2010-538723 A | 12/2010 |
| JP | 2011-194222 A | 10/2011 |
| JP | 2013-056211 A | 3/2013 |
| WO | 2009/119449 A1 | 10/2009 |

\* cited by examiner

FIG. 5B

CUFF-PRESSURE CONTROL DEVICE, CUFFED TRACHEAL TUBE, RESPIRATOR, AND OBSTRUCTION DETECTION METHOD This is a continuation of International Application No. PCT/JP2015/072032 filed on Aug. 4, 2015 which claims priority from Japanese Patent Application No. 2014-167550 filed on Aug. 20, 2014. The contents of these applications are incorporated herein by reference in their entireties.

BACKGROUND OF THE DISCLOSURE

Field of the Disclosure

The present disclosure relates to a cuff-pressure control device, a cuffed tracheal tube, a respirator, and an obstruction detection method. More specifically, the present disclosure relates to a cuff-pressure control device used for adequately maintaining the internal pressure of a cuff, a cuffed tracheal tube and a respirator including the cuff-pressure control device, and an obstruction detection method.

Description of the Related Art

In the medical field relating to a respirator and the like, tracheal intubation is known in which an operator, such as a doctor, inserts a tracheal tube in a windpipe of a subject (mainly the human body) from the oral cavity or the nasal cavity to secure the airway and oxygen is supplied to the lungs through the tracheal tube. If a gap is formed between the tracheal tube and an inner wall of the windpipe during the tracheal intubation, secretions, such as saliva and gastric juice, may flow into the windpipe, and as a result, the subject may develop the respirator associated pneumonia. To prevent such inflow of secretions, a cuff is provided on an outer wall of the tracheal tube.

A cuff is a bag-shaped member that is inflated by gas supplied therein. The gap between the tracheal tube and the inner wall of the windpipe can be closed by inflating the cuff through the supply of the gas from an air pump into the cuff through a connection path. This can prevent the secretions from flowing into the windpipe.

However, when the cuff pressure exceeds a predetermined range, the inflated cuff presses the blood vessels in the mucous tissue of the windpipe. When the blood vessels are pressed, an ischemic state is brought about, and as a result, for example, necrosis or bleeding may be caused. In contrast, when the cuff pressure falls below the predetermined range, the cuff is insufficiently inflated. Consequently, a gap is formed between an outer peripheral surface of the cuff and the inner wall of the windpipe, and secretions, such as saliva and gastric juice, sometimes flow into the windpipe.

For this reason, it is necessary to monitor and control the internal pressure of the cuff so that the internal pressure falls within the predetermined range. For example, Patent Document 1 (Japanese Unexamined Patent Application Publication No. 2011-194222) discloses a cuff-pressure control device that controls the internal pressure of a cuff so that the internal pressure falls within a predetermined range.

It is difficult to directly measure the internal pressure of the cuff disposed inside the windpipe. Hence, in normal cases, the internal pressure of the cuff is indirectly measured by measuring the internal pressure of a connection path for connecting an air pump and the cuff with a pressure sensor. For this reason, if a connection tube that forms the connection path is obstructed by, for example, bending, the internal pressure of the cuff cannot be monitored precisely. Therefore, it is preferable that the cuff-pressure control device should also have the function of detecting the obstruction of the connection tube.

When the connection tube is obstructed during the operation of the pump, the internal pressure of the connection path becomes higher than usual. Hence, one conceivable method is to detect the obstruction of the connection tube by sensing this pressure change with the pressure sensor. However, for example, when the obstruction occurs in a portion of the connection tube near the cuff, the capacity of a space (connection path) measured with the pressure sensor is decreased by only the value nearly corresponding to the capacity of the cuff, and this decrease amount is smaller than that of the capacity of the relatively long connection tube or the like. For this reason, the increase amount of the internal pressure of the connection path when obstructed is also small, and may be included in measurement errors. Therefore, there is a fear that this method cannot reliably detect the obstruction of the connection tube.

Further, Patent Document 2 (Japanese Patent No. 4175664) discloses a method for detecting the obstruction by sensing an acoustic reflected wave of a pressure pulse in a pneumatic tourniquet system. However, this system needs, for example, a pressure-pulse generating means and a reflected-wave sensing means, and this increases the size and cost of the system.

Patent Document 1: Japanese Unexamined Patent Application Publication No. 2011-194222
Patent Document 2: Japanese Patent No. 4175664

BRIEF SUMMARY OF THE DISCLOSURE

The present disclosure has been made in view of the above problems, and an object of the disclosure is to provide a cuff-pressure control device, a cuffed tracheal tube, a respirator, and an obstruction detection method that can more reliably detect the obstruction of a connection tube without increasing the size and manufacturing cost of a system.

The present inventors arrived at the present disclosure as a result of finding that the difference in internal pressure of a connection path between a time immediately after a pump stops (or an exhaust valve is closed) and a stable time after a predetermined time elapsed was large when a connection tube was not obstructed and the difference in internal pressure of the connection path was small when the connection tube was obstructed. That is, the present disclosure is as follows.

[1] A Cuff-Pressure Control Device Used for Adequately Maintaining an Internal Pressure of a Cuff, Including:

a pump that supplies gas into the cuff;

a connection path that includes a connection tube and connects the pump and the cuff;

an exhaust valve that exhausts gas in the cuff through the connection path;

a pressure sensor that measures an internal pressure of the connection path; and a controller that controls the internal pressure of the cuff by operating at least the pump or the exhaust valve according to a measured value of the internal pressure of the connection path measured with the pressure sensor, wherein the controller includes an obstruction detection unit that obtains, from the measured value of the pressure sensor, a pressure change amount from a time point when the pump is stopped while the internal pressure of the connection path is being increased by the pump or a time point where the exhaust valve is closed while the internal pressure of the connection path is being decreased by the exhaust valve to a time point after a predetermined time elapses and that detects the obstruction of the connection tube when the pressure change amount is less than or equal to a predetermined threshold value.

[2] The Cuff-Pressure Control Device According to [1],
wherein the connection tube is connected to the cuff through an inflation passage having an inner diameter smaller than an inner diameter of the connection tube, and
wherein the predetermined time is a time taken until a pressure difference between the internal pressure of the cuff and the internal pressure of the connection path is eliminated.

[3] The cuff-pressure control device according to [2], wherein the threshold value is a predetermined value less than an estimated value Px of the pressure change amount expressed by $\Delta P/(1+Vs/Vc)$ when Vc represents a capacity of the cuff, Vs represents a capacity of the connection path, and $\Delta P$ represents a pressure loss of the inflation passage.

[4] The Cuff-Pressure Control Device According to [1],
wherein the cuff has a stress at the time point when the pump is stopped or the time point when the exhaust valve is closed, and
wherein the predetermined time is a time taken until a pressure difference between the internal pressure of the cuff and the internal pressure of the connection path is eliminated.

[5] The cuff-pressure control device according to any of [1] to [4], wherein the controller gives a command to notify a warning when the obstruction detection unit detects the obstruction of the connection tube.

[6] A Cuffed Tracheal Tube Comprising:
the cuff-pressure control device according to any of [1] to [5];
a cuff; and
a tracheal tube including a main flow passage through which gas is supplied into a windpipe, and an inflation passage communicating with an inside of the cuff,
wherein the inflation passage is connected to the connection tube.

[7] A Respirator Comprising the Cuffed Tracheal Tube According to [6].

[8] An Obstruction Detection Method that Detects Obstruction of a Connection Tube in a Cuff-Pressure Control Device Used for Adequately Maintaining an Internal Pressure of a Cuff,
wherein the cuff-pressure control device includes:
a pump that supplies gas into the cuff;
a connection path that includes the connection tube and connects the pump and the cuff;
an exhaust valve that exhausts gas in the cuff through the connection path;
a pressure sensor that measures an internal pressure of the connection path; and
a controller that controls the internal pressure of the cuff by operating at least the pump or the exhaust valve according to a measured value of the internal pressure of the connection path measured with the pressure sensor, and
wherein the obstruction detection method comprises:
a calculation step of obtaining, from the measured value of the pressure sensor, a pressure change amount from a time point when the pump is stopped while the internal pressure of the connection path is being increased by the pump or a time point where the exhaust valve is closed while the internal pressure of the connection path is being decreased by the exhaust valve to a time point after a predetermined time elapses; and a detection step of detecting the obstruction of the connection tube when the pressure change amount obtained in the calculation step is less than or equal to a predetermined threshold value.

According to the present disclosure, it is possible to provide a cuff-pressure control device, a cuffed tracheal tube, a respirator, and an obstruction detection method that can more reliably detect the obstruction of a connection tube without increasing the size and manufacturing cost of a system.

BRIEF DESCRIPTION OF THE SEVERAL VIEWS OF THE DRAWINGS

FIGS. 4A and 4B include schematic graphs showing the pressure change when a cuff is pressurized in the cuff-pressure control device of the first embodiment.

FIGS. 5A and 5B include schematic graphs showing the pressure change when the cuff is depressurized in the cuff-pressure control device of the first embodiment.

FIGS. 6A and 6B include schematic views explaining the relationship between the pressure loss in an inflation tube and the pressure change in a connection path.

DETAILED DESCRIPTION OF THE DISCLOSURE

An embodiment of the present disclosure will be described below with reference to the drawings. In the drawings, the same reference numerals denote the same or corresponding portions. The dimensional relationships, such as length, width, thickness and depth, are appropriately changed to clarify and simplify the drawings, but do not show actual dimensional relationships.

First Embodiment

Figure 1:
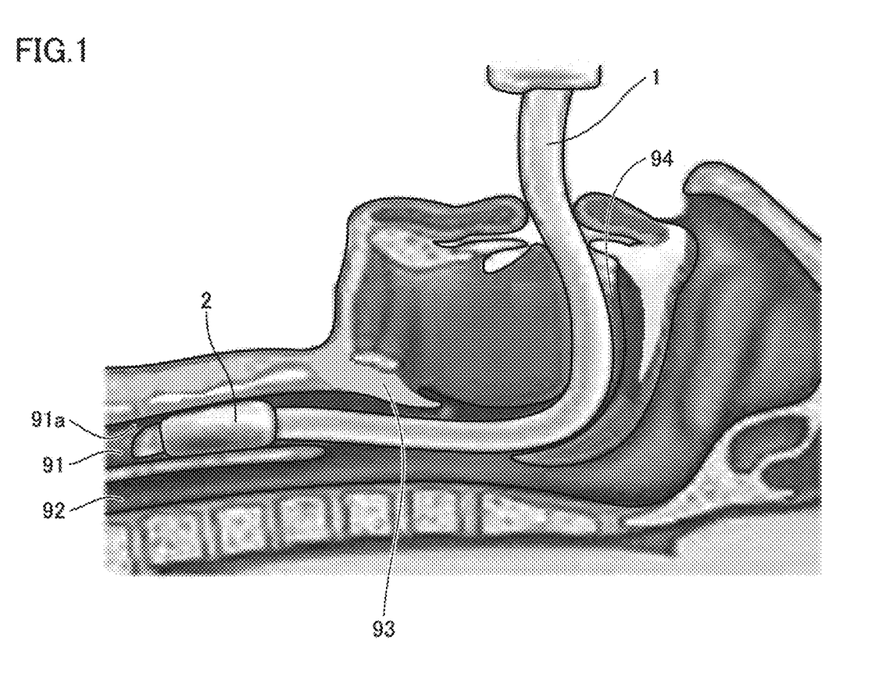
FIG. 1 schematically illustrates a state in which a tracheal tube is inserted from the oral cavity into the windpipe.

FIG. 1 schematically illustrates a state in which a tracheal tube 1 is inserted from the oral cavity into the windpipe. When the airway is secured by tracheal intubation during the use of a respirator, a tracheal tube (intratracheal tube, intubation tube) 1 is inserted from the oral cavity 94 of the subject into the windpipe 91. At this time, since the epiglottis 93 is constantly open, secretions, such as saliva, may flow into the windpipe 91 through a gap between the inserted tracheal tube 1 and an inner wall 91a of the windpipe 91, and as a result, the subject may develop respirator associated pneumonia (VAP).

To prevent such inflow of secretions, a cuff 2 is provided at a predetermined position on an outer periphery of the tracheal tube 1. The cuff 2 can be inflated by air supplied from the outside of the body through an air supply tube (not illustrated) to be described later. When the cuff 2 is inflated, an outer peripheral surface of the cuff 2 comes into contact with the inner wall 91a of the windpipe 91, and closes the gap between the tracheal tube 1 and the inner wall 91a of the windpipe 91. By using such a cuffed tracheal tube, the tracheal tube 1 can secure an airway, and the cuff 2 can prevent secretions and the like from flowing into the windpipe 91.

In this case, the internal pressure of the cuff 2 (cuff pressure) needs to be maintained adequately. If the cuff pressure is low, a gap is formed between the tracheal tube 1 and the inner wall 91a of the windpipe 91. In contrast, if the cuff pressure is too high, the blood flow in the respiratory tract mucous membrane is impeded and the respiratory tract mucous membrane is damaged. For example, when the cuff is a low-pressure and large-capacity cuff, an adequate cuff pressure is about 20 to 30 cm $H_2O$.

In the present disclosure, the term "cuff" refers to a bag-shaped member whose inside can have a predetermined pressure by being filled with a predetermined amount of gas. The member is not particularly limited as long as the internal pressure thereof can be adjusted, and includes not only the member generally called a cuff, but also, for example, a balloon of a balloon catheter.

Figure 2:
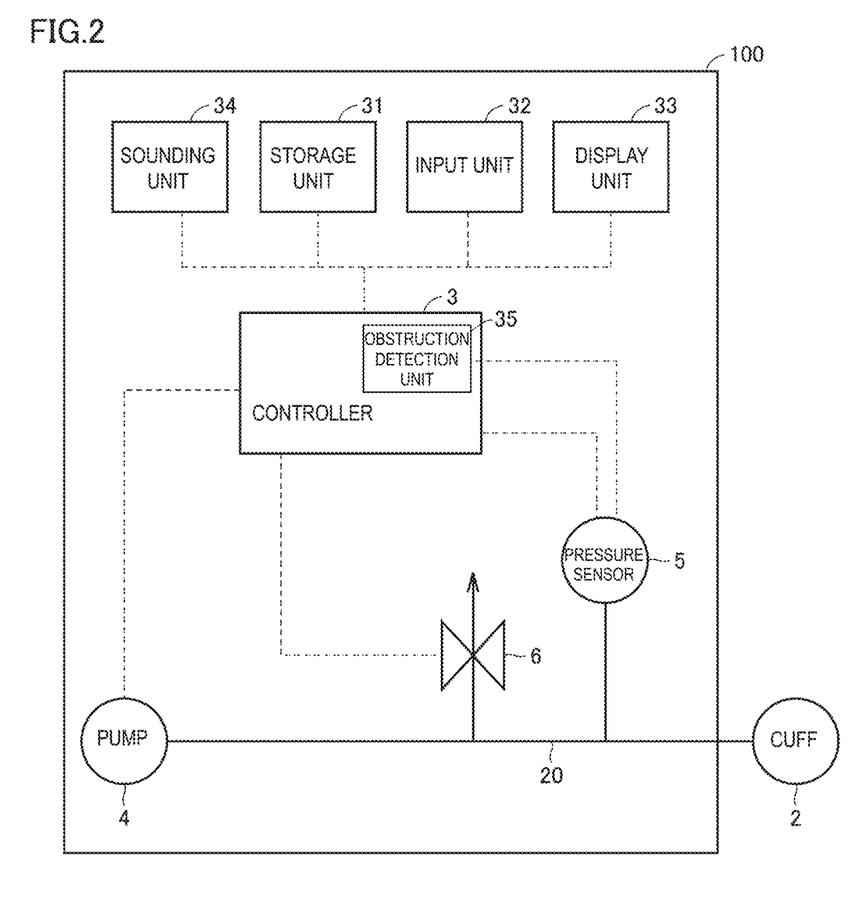
FIG. 2 is a block diagram illustrating the configuration of the principal part of a cuff-pressure control device according to a first embodiment.

FIG. 2 is a block diagram illustrating the configuration of a principal part of a cuff-pressure control device according to the first embodiment of the present disclosure. A cuff-pressure control device 100 is connected to the cuff 2 through a connection path (a flow passage for gas such as air) shown by a solid line in the figure. The internal pressure of the cuff 2 (cuff pressure) is controlled to the above-described adequate value by the cuff-pressure control device 100.

The cuff-pressure control device 100 mainly includes a controller 3, a pump 4, a pressure sensor 5 for measuring the cuff pressure, and an exhaust valve 6. The controller 3 includes an obstruction detection unit 35.

The controller 3 compares a setting range registered in a storage unit 31 (the setting range can be changed in an input unit 32) with the cuff pressure measured with the pressure sensor 5, and controls the operation of at least the pump 4 or the exhaust valve 6 according to the pressure difference therebetween. However, the pressure sensor 5 directly measures the internal pressure of the connection path (a connection pipe 20), and thereby indirectly measures the internal pressure of the cuff 2 (cuff pressure). For example, the controller 3 is formed by a microcontroller (MCU).

Specifically, when the cuff pressure is lower than the setting range, the pump 4 is driven to supply air into the cuff 2 and to thereby increase the cuff pressure. At this time, the exhaust valve 6 is closed in an N.C. (normal closed) state. When the cuff pressure increases and returns into the setting range, the pump 4 is stopped.

On the other hand, for example, when the diameter of the windpipe is changed by the change of the posture of a patient, the cuff pressure sometimes exceeds the setting range. When the cuff pressure thus exceeds the setting range, the exhaust valve 6 is opened to exhaust air from the inside of the cuff 2 and to thereby decrease the cuff pressure. When the cuff pressure decreases and returns into the setting range, the exhaust valve 6 is closed. In this way, the controller 3 controls the pump 4 and the exhaust valve 6 so that the cuff pressure falls within the setting range.

Although the pump 4 is not particularly limited, a piezoelectric pump is preferably used in the point that it allows easy fine adjustment of the supply amount of air into the cuff. While an air tube connected to the pump 4 may be provided with a check valve for maintaining the pressure inside the cuff when the pump 4 is stopped, it is not particularly necessary when the pump itself has the non-return function.

While the exhaust valve 6 is not particularly limited, for example, an electromagnetic valve (solenoid valve) can be used.

The obstruction detection unit 35 obtains, from the measured value of the pressure sensor 5, the pressure change amount from a time point when the pump 4 is stopped while the internal pressure of the connection path is being increased by the pump 4 or from a time point when the exhaust valve 6 is closed while the internal pressure of the connection path is being decreased by the exhaust valve 6 to a time point after a predetermined time elapses. Then, the obstruction detection unit 35 compares the obtained pressure change amount (absolute value) with a threshold value registered in a storage unit 31 (the threshold value can be changed in the input unit 32), and detects the obstruction of a connection tube 21 (connection path) when the pressure change amount is less than or equal to the predetermined threshold value.

A display unit 33 displays, for example, the measured cuff pressure (internal pressure of the connection tube), the setting range of the cuff pressure, and the above-described threshold value of the pressure change amount. A sounding unit 34 sounds a warning when some abnormality occurs (for example, when the connection tube is obstructed). The controller 3 gives a command to the display unit 33 and the sounding unit 34 to notify a warning when the obstruction detection unit 35 detects the obstruction of the connection tube. Such notification of the warning can urge a medical staff or the like to perform operations such as removal of obstruction of the connection tube.

Figure 3A:
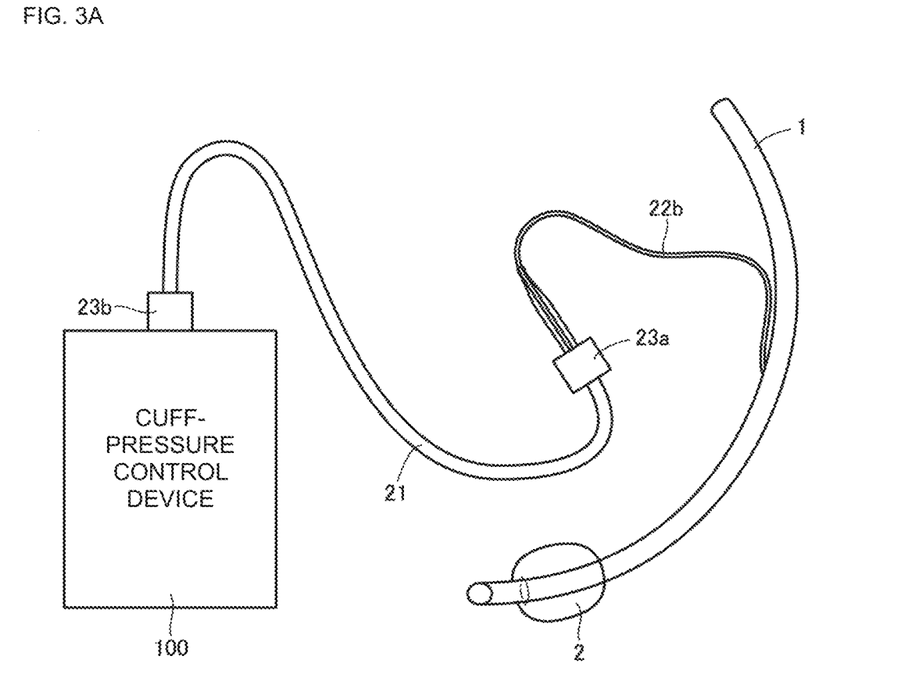
FIG. 3A schematically illustrates a cuffed tracheal tube provided with the cuff-pressure control device of the first embodiment.
Figure 3B:
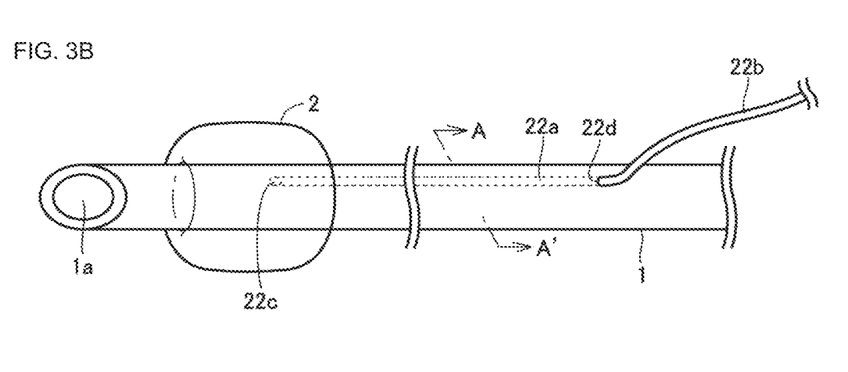
FIG. 3B is an enlarged schematic view of a distal end portion of the cuffed tracheal tube illustrated in FIG. 3A.
Figure 3C:
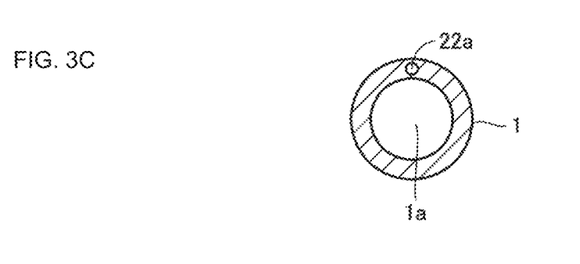
FIG. 3C is a schematic cross-sectional view taken along line A-A' of FIG. 3B.

FIG. 3A is a schematic view of a cuffed tracheal tube provided with the cuff-pressure control device of this embodiment. FIG. 3B is an enlarged schematic view of a distal end portion of the cuffed tracheal tube illustrated in FIG. 3A. FIG. 3C is a schematic cross-sectional view taken along line A-A' of FIG. 3B.

In the cuffed tracheal tube of this embodiment, an inflation passage communicating with the inside of the cuff 2 provided on the tracheal tube 1 is connected to the cuff-pressure control device 100 through the connection tube 21. One end portion of the connection tube 21 is connected to the inflation passage (inflation tube 22b) by a luer connector 23a. The other end portion of the connection tube 21 is connected to the connection pipe 20 (FIG. 2) inside the cuff-pressure control device 100 by a luer connector 23b.

In this way, the connection path for connecting the pump 4 and the cuff 2 is composed of the connection pipe 20, the connection tube 21, and the inflation passage 22 (a flow passage 22a and the inflation tube 22b). The cuff 2, the connection tube 21, the inflation tube 22b, and the tracheal tube 1 are formed of, for example, polyvinyl chloride or olefin-based elastomer.

Here, the inflation passage is composed of the flow passage 22a (FIGS. 3B and 3C) and the inflation tube 22b (FIG. 3A). As illustrated in FIG. 3C, the flow passage 22a is provided in parallel with a main flow passage 1a of the tracheal tube 1 in a wall portion that defines the main flow passage 1a, but does not communicate with the main flow passage 1a of the tracheal tube 1. The flow passage 22a communicates with the inside of the cuff 2 through a hole 22c opening in an outer side portion of the tracheal tube 1. The flow passage 22a also communicates with the inside of the inflation tube 22b through a hole 22d opening in the outer side portion of the tracheal tube 1. The inner diameter of such an inflation passage (inflation tube 22b and flow passage 22a) is smaller than the inner diameter of the connection tube 21.

Figure 4A:
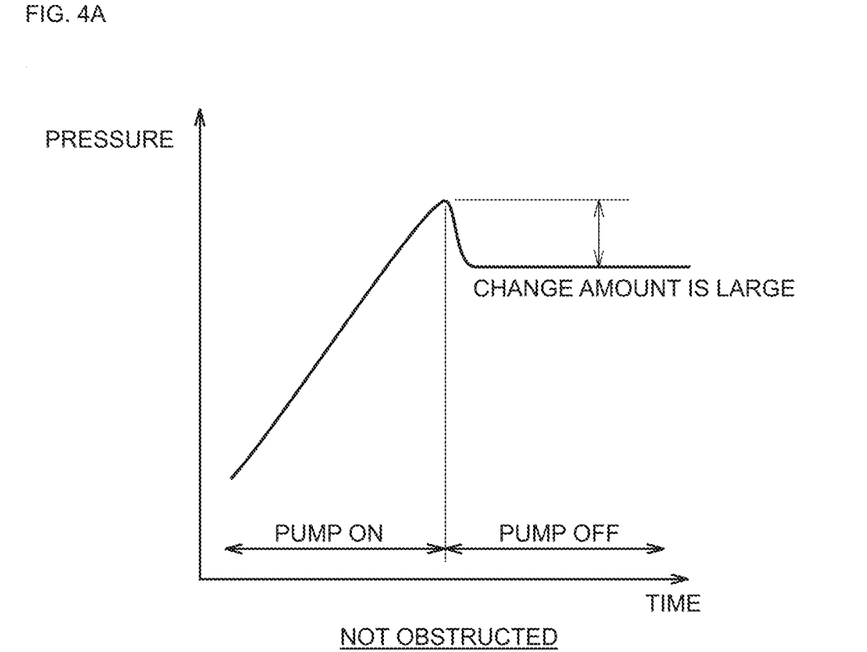
FIG. 4A shows the pressure change when a connection tube is not obstructed and FIG. 4B shows the pressure change when the connection tube is obstructed.
Figure 4B:
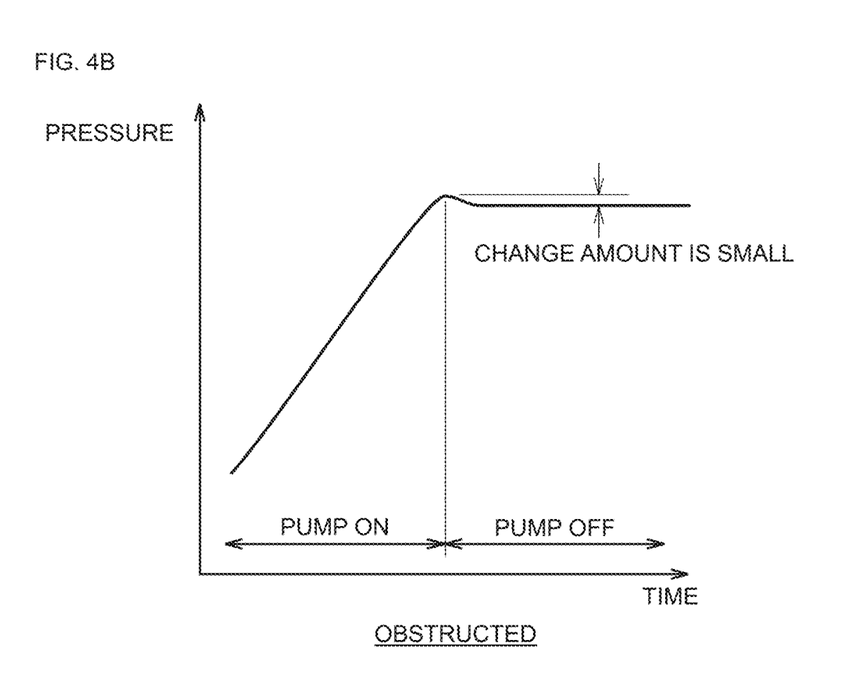

FIGS. 4A and 4B include schematic graphs showing the pressure change in the connection path when the cuff is pressurized in the cuff-pressure control device of the first embodiment. FIG. 4A shows the pressure change in the connection path when the connection tube is not obstructed and FIG. 4B shows the pressure change in the connection path when the connection tube is obstructed. When the connection tube is not obstructed, as shown in FIG. 4A, the pressure decreases immediately after the pump stops, and is stabilized after a predetermined time elapses. At this time, the predetermined time is, for example, one second or less.

In contrast, when the connection tube is obstructed, as shown in FIG. 4B, the pressure decrease amount (pressure change amount) after the stop of the pump is small. For this reason, the obstruction detection unit 35 can detect the obstruction of the connection tube 21 by sensing such a difference in the pressure change amount during the pressurization of the cuff.

Figure 5A:
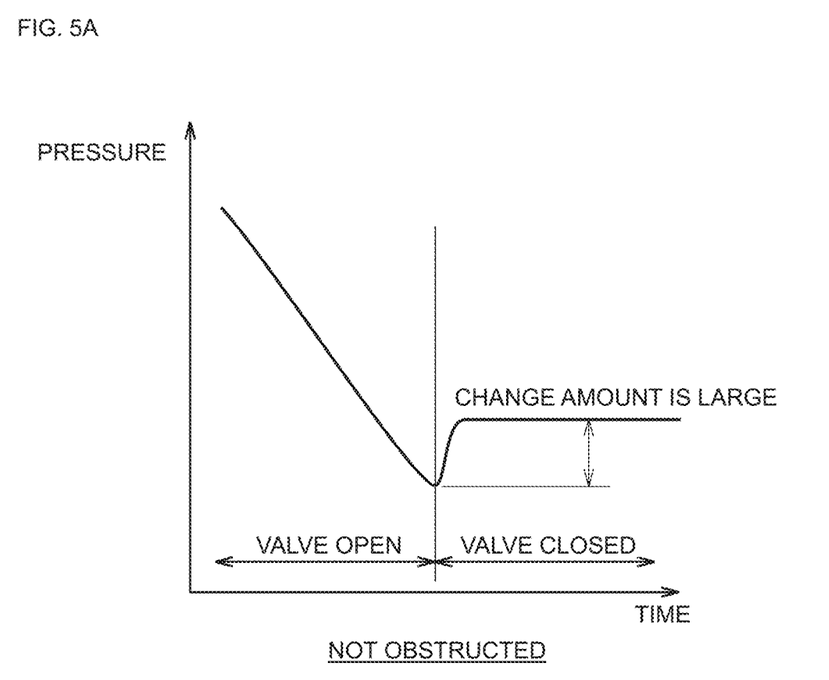
FIG. 5A shows the pressure change when the connection tube is not obstructed and FIG. 5B shows the pressure change when the connection tube is obstructed.
Figure 5B:
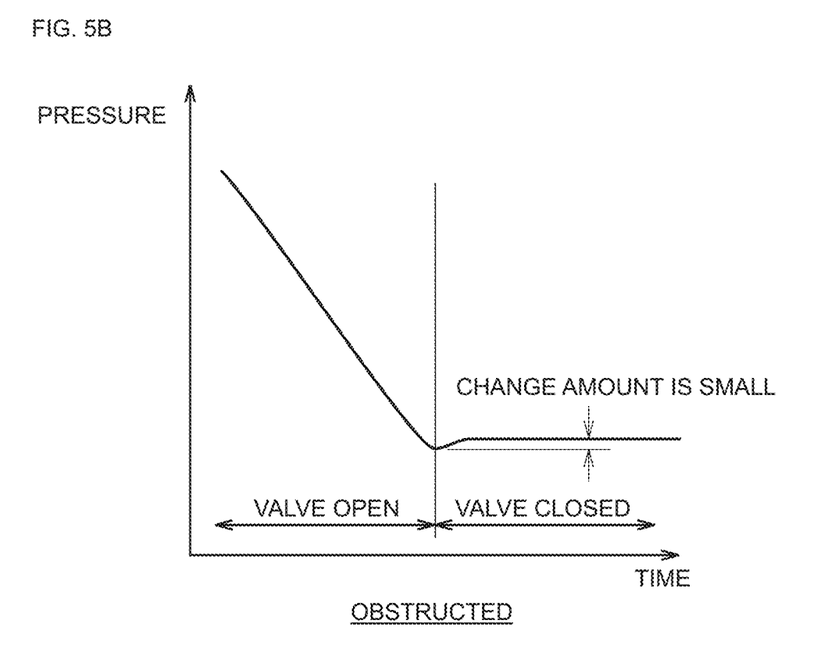

FIGS. 5A and 5B include schematic graphs showing the pressure change in the connection path when the cuff is depressurized in the cuff-pressure control device of the first embodiment. As shown in FIGS. 5A and 5B, when the connection tube is obstructed during the depressurization of the cuff (FIG. 5B), the pressure increase amount (pressure change amount) of the connection path after the exhaust valve is closed is smaller than when the connection tube is not obstructed (FIG. 5A). For this reason, during depressurization of the cuff, the obstruction detection unit 35 can also detect obstruction of the connection tube 21 by sensing such a difference in the pressure change amount.

Here, a description will be given of the reason why the pressure change amount differs according to the presence or absence of obstruction. Roughly, two factors are conceivable. The first factor is the change in pressure loss. Mainly referring to FIG. 6A, as described above, the flow passage 22a that constitutes the inflation passage 22 communicating with the cuff 2 is provided in the wall portion that defines the main flow passage 1a of the tracheal tube 1, and its space is limited. For this reason, the inner diameter of the inflation passage 22 is about 1 mm, and this is considerably small. In contrast, the inner diameter of the connection tube 21 is about 2 mm, and this is large. Since the pressure loss of the flow in the tube is generally inversely proportional to the fourth power of the diameter, the pressure loss in the inflation passage 22 is dominant in the gas flow passage (connection path) from the pump 4 to the cuff 2.

Figure 6A:
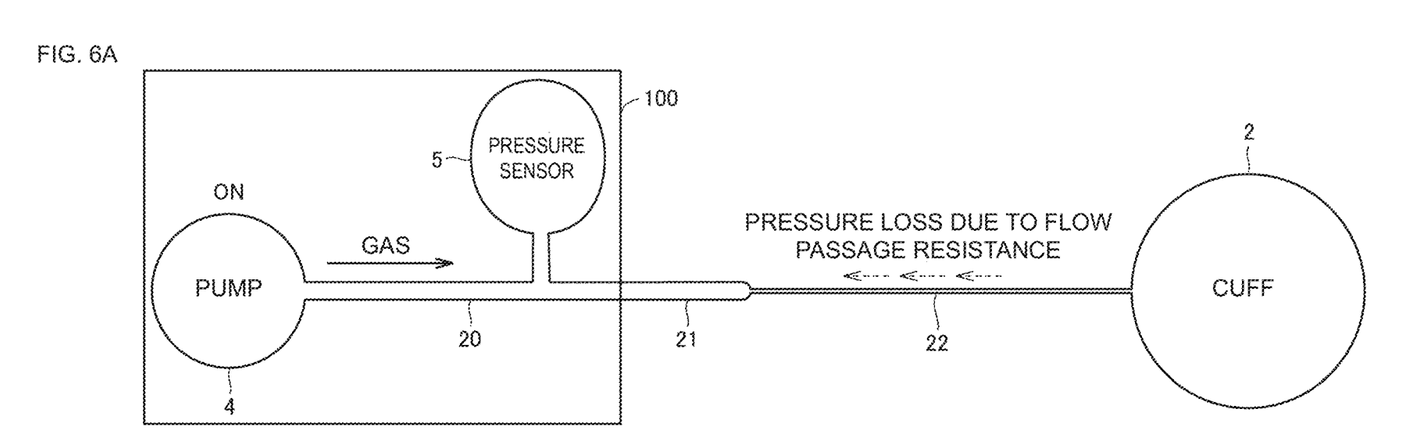
FIG. 6A illustrates a state in which a difference is formed between the internal pressure of the connection path and the internal pressure of the cuff by the pressure loss.

When the connection tube 21 is not obstructed and the cuff 2 is pressurized (or depressurized), an air flow is produced between the pump 4 and the cuff 2. Since there is pressure loss in the inflation passage 22, a pressure difference corresponding to the pressure loss is formed between the connection path (mainly, the connection pipe 20 and the connection tube 21) and the cuff 2. However, when the pump is stopped (or the valve is closed), the pressure difference is eliminated and an equilibrium state is brought about. That is, while the internal pressure of the connection path is higher than the internal pressure of the cuff 2 by the amount corresponding to the pressure loss during the pressurization (during the operation of the pump 4), when the pump 4 is stopped, the amount of gas corresponding to the pressure difference flows into the cuff 2 and brings about a pressure equilibrium state. Hence, the internal pressure of the connection path decreases.

When the exhaust valve 6 is opened and gas inside the cuff 2 is exhausted to depressurize the cuff 2, similarly except that the direction of the flow of gas is opposite, after the exhaust valve 6 is closed, the amount of gas corresponding to the pressure difference flows from the cuff 2 into the connection path and brings about a pressure equilibrium state. Hence, the internal pressure of the connection path increases.

Further, since the inflation passage 22 is generally shorter than the connection tube 21, it is unlikely to be obstructed. Moreover, since the curvature radius of the cross-sectional shape thereof is small, obstruction rarely occurs.

The second factor is the difference in rigidity between the cuff 2 and the constituent materials (tubes) of the connection path. Mainly referring to FIG. 6B, the cuff 2 is formed by a considerably thin resin film, and the connection tube 21 that constitutes the exhaust path is much thicker than the cuff 2. For this reason, when the connection tube 21 is obstructed, the total rigidity in a space 200 (the connection path and the cuff 2) whose internal pressure is measured by the pressure sensor 5 is changed greatly.

Figure 6B:
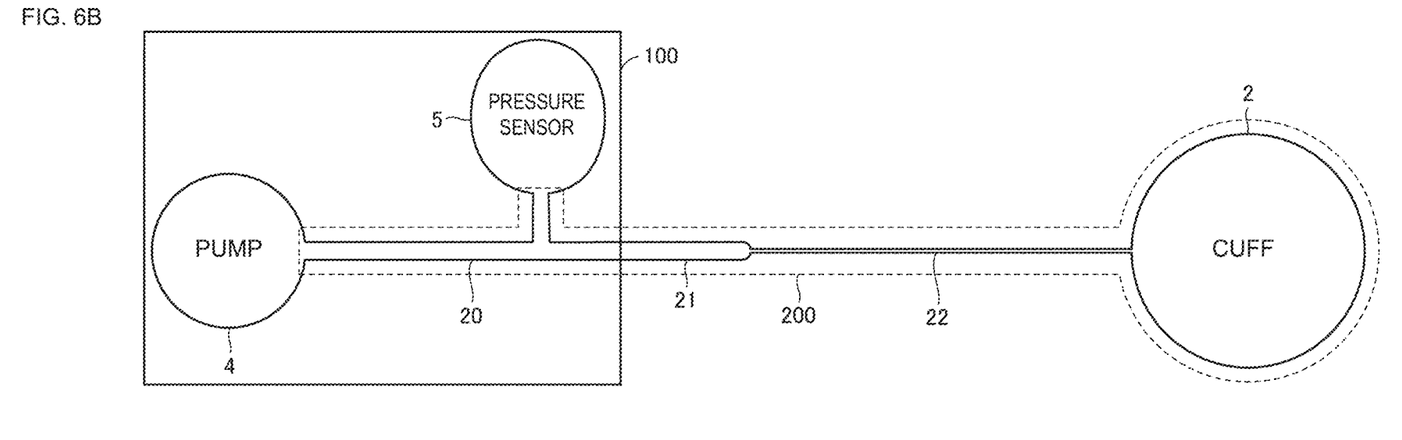
FIG. 6B illustrates a state in which the influence of the pressure loss is removed and the internal pressure of the connection path and the internal pressure of the cuff become equal to each other.

For this reason, when the connection tube 21 is not obstructed, the rigidity at the cuff 2 is low, and the influence of viscosity of the resin serving as a viscoelastic material is large. Hence, stress (stress for pushing out gas in the cuff 2) is generated by the pressurization of the cuff 2. For this reason, after the pump 4 is stopped, the stress is relaxed, and simultaneously, the cuff 2 inflates. Consequently, the internal pressure of the connection path decreases, and becomes stable after a predetermined time elapses. At this time, the predetermined time is, for example, 10 seconds or less.

In contrast, when the connection tube is obstructed, the rigidity of the flow passage increases and the influence of viscosity decreases. Hence, such stress is not generated, and the pressure change amount after the pump 4 is stopped is small. By detecting such difference in pressure change amount, the obstruction of the connection tube 21 can be detected even when the connection path does not have a portion where the pressure loss occurs, as in the inflation passage 22. Hence, the obstruction can be more stably detected.

The threshold value is preferably set at a predetermined value less than an estimated value Px of the pressure change amount. The threshold value is more preferably set, for example, at 20% to 90% of Px. Thus, the threshold value can be optimized by using Px as a guide, and the obstruction can be more stably detected. However, Px does not always need to be used as the guide, and the threshold value may be set by a preliminary test conducted beforehand.

In the case in which the connection tube is connected to the cuff through the inflation passage having an inner diameter smaller than that of the connection tube, as in the embodiment (the inflation passage 22 has pressure loss at the time point when the pump 4 is stopped or the time point when the exhaust valve 6 is closed), the predetermined time in which the pressure change amount is measured is the time taken until the pressure difference between the internal pressure of the cuff 2 and the internal pressure of the connection path is eliminated, the estimated value Px of the pressure change amount is expressed by $\Delta P/(1+Vs/Vc)$ where Vc represents the capacity of the cuff 2, Vs represents the capacity of the connection path, and $\Delta P$ represents the pressure loss of the inflation passage 22. The capacity Vs of the connection path may be the capacities of the connection pipe 20 and the connection tube 21 without considering the capacity of the inflation passage 22.

This estimated value Px is found using a state equation of an ideal gas. That is, $Ps_1=Pc+\Delta P$ [Equation 1] where $Ps_1$ represents the internal pressure of the connection path (the connection pipe 20 and the connection tube 21) and Pc represents the internal pressure of the cuff 2 before the pump is stopped. Here, the state quantity before the pump is stopped (in a dynamic equilibrium state) is $Ps_1 Vs+PcVc$. By substituting Equation 1 in this, the state quantity becomes $Ps_1(Vs+Vc)-\Delta PVc$ [Equation 2].

On the other hand, when the internal pressure of the connection path (the connection pipe 20 and the connection tube 21) in the state in which the pressure in the connection path is stabled after the stop of the pump (in a static equilibrium state) is taken as $Ps_2$, the state quantity in the static equilibrium state is $Ps_2(Vs+Vc)$[Equation 3]. Here, since the change in cuff capacity Vc is small, it is ignored, and the cuff capacity Vc is fixed. Since the state quantity is fixed in the dynamic equilibrium state and the static equilibrium state, Equation 2 equals Equation 3, that is, $Ps_1(Vs+Vc)-\Delta PVc=Ps_2(Vs+Vc)$. Thus, the pressure change amount $(Ps_1-Ps2)$ is $\Delta P/(1+Vs/Vc)$.

It should be considered that the embodiment disclosed herein is illustrative in all respects and is not restrictive. The scope of the present disclosure is shown not by the above description but by the scope of the claims, and it is intended to include all modifications within the meaning and scope equivalent to the scope of claims.

100: cuff-pressure control device, 1: tracheal tube, 1a: main flow passage, 2: cuff, 20: connection pipe, 21: connection tube, 22: inflation passage, 22a: flow passage, 22b: inflation tube, 22c, 22d: hole, 23a, 23b: luer connector, 200: internal space, 3: controller, 31: storage unit, 32: input unit, 33: display unit, 34: sounding unit, 4: pump, 5: pressure sensor, 6: exhaust valve, 91: windpipe, 91a: inner wall, 92: esophagus, 93: epiglottis, 94: oral cavity.

The invention claimed is:

1. A cuff-pressure control device used for adequately maintaining an internal pressure of a cuff, the cuff-pressure control device comprising:
   a pump for supplying gas into the cuff;
   a connection path including a connection tube and for connecting the pump to the cuff;
   an exhaust valve for exhausting the gas in the cuff through the connection path;
   a pressure sensor for measuring an internal pressure of the connection path; and
   a controller for controlling the internal pressure of the cuff by operating at least the pump or the exhaust valve according to a measured value of the internal pressure of the connection path measured with the pressure sensor,
   wherein the controller is configured to detect obstructions via obtaining, from the measured value of the pressure sensor, a pressure change amount from a time point when the pump is stopped while the internal pressure of the connection path is being increased due to the pump or from a time point where the exhaust valve is closed while the internal pressure of the connection path is being decreased due to the exhaust valve to a time point after a predetermined time elapses and detecting an obstruction of the connection tube when the pressure change amount is less than or equal to a predetermined threshold value.

2. The cuff-pressure control device according to claim 1, wherein the connection tube is connectable to the cuff through an inflation passage having an inner diameter smaller than an inner diameter of the connection tube.

3. The cuff-pressure control device according to claim 2, wherein the predetermined threshold value is a predetermined value less than an estimated value Px of the pressure change amount expressed by $\Delta P/(1+Vs/Vc)$ wherein Vc represents a capacity of the cuff, Vs represents a capacity of the connection path, and $\Delta P$ represents a pressure loss of the inflation passage.

4. The cuff-pressure control device according to claim 1, in combination with the cuff,
   wherein the cuff has a stress at the time point when the pump is stopped or the time point when the exhaust valve is closed, and
   wherein the predetermined time is a time taken until a pressure difference between the internal pressure of the cuff and the internal pressure of the connection path is eliminated.

5. The cuff-pressure control device according to claim 1, wherein the controller is configured to give a command to notify a warning when the obstruction of the connection tube is detected.

6. A cuffed tracheal tube comprising:
   the cuff-pressure control device according to claim 1;
   the cuff; and
   a tracheal tube including a main flow passage through which gas is supplied into a windpipe, and an inflation passage communicating with an inside of the cuff,
   wherein the inflation passage is connected to the connection tube.

7. A respirator comprising the cuffed tracheal tube according to claim 6.

8. An obstruction detection method for detecting obstruction of a connection tube in a cuff-pressure control device used for adequately maintaining an internal pressure of a cuff,
   wherein the cuff-pressure control device includes:
   a pump for supplying gas into the cuff;
   a connection path including the connection tube and for connecting the pump to the cuff;
   an exhaust valve for exhausting the gas in the cuff through the connection path;
   a pressure sensor for measuring an internal pressure of the connection path; and
   a controller for controlling the internal pressure of the cuff by operating at least the pump or the exhaust valve according to a measured value of the internal pressure of the connection path measured with the pressure sensor,
   the obstruction detection method comprising:
   a calculation step of obtaining, from the measured value of the pressure sensor, a pressure change amount from a time point when the pump is stopped while the internal pressure of the connection path is being increased due to the pump or from a time point where the exhaust valve is closed while the internal pressure of the connection path is being decreased due to the exhaust valve to a time point after a predetermined time elapses; and
   a detection step of detecting the obstruction of the connection tube when the pressure change amount obtained in the calculation step is less than or equal to a predetermined threshold value.

9. The cuff-pressure control device according to claim 2, wherein the controller is configured to give a command to notify a warning when the obstruction of the connection tube is detected.

10. The cuff-pressure control device according to claim 3, wherein the controller is configured to give a command to notify a warning when the obstruction of the connection tube is detected.

11. The cuff-pressure control device according to claim 4, wherein the controller is configured to give a command to notify a warning when the obstruction of the connection tube is detected.

12. A cuffed tracheal tube comprising:
the cuff-pressure control device according to claim 2;
the cuff; and
a tracheal tube including a main flow passage through which gas is supplied into a windpipe, and an inflation passage communicating with an inside of the cuff,
wherein the inflation passage is connected to the connection tube.

13. A cuffed tracheal tube comprising:
the cuff-pressure control device according to claim 3;
the cuff; and
a tracheal tube including a main flow passage through which gas is supplied into a windpipe, and an inflation passage communicating with an inside of the cuff,
wherein the inflation passage is connected to the connection tube.

14. A cuffed tracheal tube comprising:
the cuff-pressure control device according to claim 4;
the cuff; and
a tracheal tube including a main flow passage through which gas is supplied into a windpipe, and an inflation passage communicating with an inside of the cuff,
wherein the inflation passage is connected to the connection tube.

15. A cuffed tracheal tube comprising:
the cuff-pressure control device according to claim 5;
the cuff; and
a tracheal tube including a main flow passage through which gas is supplied into a windpipe, and an inflation passage communicating with an inside of the cuff,
wherein the inflation passage is connected to the connection tube.

* * * * *

UNITED STATES PATENT AND TRADEMARK OFFICE
CERTIFICATE OF CORRECTION

PATENT NO. : 10,716,913 B2
APPLICATION NO. : 15/431949
DATED : July 21, 2020
INVENTOR(S) : Higashiyama et al.

It is certified that error appears in the above-identified patent and that said Letters Patent is hereby corrected as shown below:

In the Specification

Column 9, Line 36, "tracheal tube, la:" should be -- tracheal tube, 1a: --.

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*